United States Patent [19]

Gruss et al.

[11] Patent Number: 5,747,250
[45] Date of Patent: May 5, 1998

[54] PROBE FOR TUMOUR DIAGNOSTICS OR TUMOUR THERAPY

[75] Inventors: Peter Gruss, Göttingen, Germany; Catharina Maulbecker, Zürich, Switzerland

[73] Assignee: Max-Planck-Gesellschaft zur Forderung der Wissenschaften e.V., Berlin, Germany

[21] Appl. No.: 381,841

[22] PCT Filed: Aug. 2, 1993

[86] PCT No.: PCT/EP93/02051

§ 371 Date: Mar. 27, 1995

§ 102(e) Date: Mar. 27, 1995

[87] PCT Pub. No.: WO94/03196

PCT Pub. Date: Feb. 17, 1994

[30] Foreign Application Priority Data

Aug. 3, 1992 [DE] Germany ................. 42 25 569.4

[51] Int. Cl.⁶ ............... C12Q 1/68; C12P 19/34; C07H 21/02; C07H 21/04

[52] U.S. Cl. ............... 435/6; 435/7.1; 435/7.23; 435/7.9; 435/91.2; 435/174; 435/287.2; 536/23.1; 536/24.3; 536/24.33; 530/388.1

[58] Field of Search ............... 435/6, 7.1, 7.9, 435/91.2, 7.23, 287.2, 174; 536/23.1, 24.3, 24.33; 530/388.1

[56] References Cited

PUBLICATIONS

Frazier et al. J. Cell Physiol 133: 169–174 (abstract), 1987.
Ishiwata et al. Exp. Pathology 41: 1–9 (abstract), 1991.
Dressler et al PNAS 89 1179–1183, 1992.

*Primary Examiner*—W. Gary Jones
*Assistant Examiner*—Dianne Rees
*Attorney, Agent, or Firm*—Felfe & Lynch

[57] ABSTRACT

A therapeutic or diagnostic agent according to the invention contains as the active substance at least one nucleic acid which hybridizes with a Pax gene or at least one Pax protein or at least one antibody against a Pax protein or a derivative thereof. The agents according to the invention are used in tumour diagnosis or/and tumour therapy as well as an antisense nucleic acid for the inhibition of gene expression.

13 Claims, 2 Drawing Sheets

PROBE FOR TUMOUR DIAGNOSTICS OR TUMOUR THERAPY

FIELD OF THE INVENTION

The present invention concerns a new therapeutic or diagnostic agent which contains at least one nucleic acid as the active substance and is particularly suitable for the diagnosis or/and therapy of tumours. Diagnostic and therapeutic methods using these materials are also features of the invention.

BACKGROUND AND PRIOR ART

Proteins which contain a homeobox play an important role in the development of multicellular differentiated tissue. It is assumed that transcriptional regulation by the homeobox proteins coordinates the exact spatial and chronological sequence of growth and differentiation in the developing embryo. It is known from the literature (see e.g. K. Kongsuwan, J. M. Adams, Nucleic Acids Res. 17 (1989), 1881–1891; C. Blatt, D. Aberdam, R. Schwartz, L. Sachs, EMBO J. 7 (1988), 4283–4290; C. Blatt, Cancer Cells 2 (1990), 186–189; T. H. Rabbitts Cell 647 (1991), 641–644; A. W. Sasaki, J. Doskow, C. L. Macleod, M. B. Rodgers, L. J. Goudas, M. F. Wilkinson, MOD34 (1991), 155–164)) that some genes containing a homeobox are connected with oncogenesis.

A multigene family which has a common conserved sequence motif, the "paired"-box, is also connected with developmental control and tissue specificity in various organisms. The "paired" domain coded by the "paired" box represents a DNA-binding domain (J. Treisman, E. Harris, C. Desplan, Genes. Dev. 5 (1991), 594–604; G. Chalepakis, R. Fritsch, H. Fickenscher, 0. Deutsch, M. Goulding, P. Gruss, Cell 66 (1991), 873–884) and has been identified in various organisms such as Drosophila, mouse, tortoise, zebra fish, nematodes and humans. There has not yet been known to be a connection between the "paired" domain and oncogenesis. Great efforts are made in medical research to provide new therapeutic and diagnostic agents related to the development of tumours. The object of the present invention is to provide a new agent which is particularly suitable for the diagnosis and therapy of tumours.

SUMMARY OF THE INVENTION

The object according to the invention is achieved by a process for the production of an agent for tumour diagnostics or/and tumour therapy and methods of using the agent, wherein the agent is characterized in that it comprises (a) at least one nucleic acid molecule which hybridizes with a Pax gene (b) at least one Pax protein or/and (c) at least one antibody against a Pax protein or a derivative thereof If desired together with common pharmaceutical carrier substances, auxiliary substances and diluents.

Surprisingly it was found that Pax proteins, i.e. proteins which contain the "paired" domain, can promote oncogenesis and can therefore be classified as a new group of strong oncoproteins which induce cell proliferation, anchor-independent growth and angiogenesis. It was found that cells transformed with Pax genes exhibit all the classical signs of malignancy such as e.g. contact inhibition in the focus assay, growth in soft agar and tumour induction in the nude mouse.

The therapeutic or diagnostic agent according to the invention can therefore be used as a molecular probe in tumour diagnostics since the use of a nucleic acid which hybridizes with a nucleotide sequence coding for a Pax protein enables a qualitative and quantitative, cell- and tissue-specific determination of the expression of the respective Pax gene.

However, the agent according to the invention is also suitable as an antisense nucleic acid for the specific inhibition of the expression of genes which contain the Pax sequence and is thus also suitable as a therapeutic agent.

For a diagnostic test or/and for a therapeutic treatment an agent according to the invention must contain at least one nucleic acid molecule which hybridizes to a Pax gene. The nucleic acid according to the invention preferably hybridizes under "stringent conditions" to a Pax gene. Stringent conditions within the meaning of the present invention are defined as those conditions that enable a selective and detectable specific binding of the nucleic acid to a particular Pax gene or to several Pax genes or Pax transcripts. Such a hybridization under stringent conditions preferably means that binding of the probe to the Pax gene or to the Pax RNA is still detectable after hybridization at 68° C. in an aqueous solution or at 42° C. in 50% formamide and subsequent washing of the filter at 65° C. in an aqueous solution.

The therapeutic or diagnostic agent according to the invention preferably contains as an active substance at least one nucleic acid molecule which comprises (a) the nucleotide sequence coding for a Pax protein, (b) a part thereof, (c) a nucleotide sequence hybridizing under stringent conditions (see above) with a nucleic acid from (a) or/and (b) or (d) a nucleotide sequence complementary to a nucleic acid from (a), (b) or/and (c). If it is desired that the nucleic acid molecule according to the invention should originate from a conserved region of the Pax gene, i.e. from the nucleotide sequence coding for the "paired" domain, it is preferable to use a nucleic acid which comprises (a) a nucleotide sequence coding for the amino acids 1 to 74 of the "paired"domain, (b) a part thereof, (c) a nucleotide sequence hybridizing under stringent conditions with a nucleic acid from (a) or/and (b) or (d) a nucleotide sequence complementary to a nucleic acid from (a), (b) or/and (c).

In a further preferred embodiment for the above purpose the agent according to the invention contains at least one nucleic acid which comprises (a) a nucleotide sequence coding for the amino acids 5 to 19, 35 to 41, 68 to 74, 95 to 100 or/and 115 to 120 of a "paired"domain, (b) a part thereof, (c) a nucleotide sequence hybridizing under stringent conditions with a nucleic acid from (a) or/and (b) or (d) a nucleotide sequence complementary to a nucleic acid from (a), (b) or/and (c).

The aforementioned nomenclature for the amino acids complies in this case with the publication of Walther et al., Genomics 11 (1991), 424–434 in particular FIG. 2 which hereby becomes by reference a part of the description.

If it is, however, necessary to specifically detect or inhibit a single Pax gene, it is expedient to use a nucleic acid molecule with a nucleotide sequence from a non-conserved region of the respective gene i.e. preferably from the region which does not code for the "paired"domain.

The agent according to the invention contains a nucleic acid which is derived from any desired Pax gene. Examples of suitable Pax genes are Pax-1 (Deutsch et al., Cell 53 (1988), 617–625), Pax-2 (Dressler et al., Development 109 (1990), 787–795; Nornes et al., Development 109 (1990), 797–809), Pax-3 (Goulding et al., EMBO J. 10 (1991), 1135–1147), Pax-4, Pax-5 and Pax-6 (Walther et al. (1991), supra), Pax-7 (Jostes et al., MOD 33 (1990), 27–38), Pax-8 (Plachov et al., Development 110 (1990), 643–651), HuP1, HuP2, HuP48 (Burri et al., EMBO J. 8 (1989), 1183–1190), prd, BSH4 and BSH9 (Bopp et al., Cell 47 (1986), 1033–1040) and Pox neuro and Pox meso (Bopp et al., EMBO J. 8 (1989), 3447–3457). The aforementioned literature references become by reference part of the description. Human Pax genes are particularly preferred.

The nucleic acid molecule in the agent according to the invention is—depending on the requirement—preferably an unmodified or modified DNA or RNA. The length of the nucleic acid molecule also depends on the respective area of application.

If the agent according to the invention is used as a molecular probe in tumour diagnostics, it is preferably a DNA probe with a length of 10 to 100 nucleotides, preferably 12 to 50 nucleotides. Furthermore it is preferred that the nucleic acid molecule carries a radioactive or non-radioactive label which serves to detect the binding to a Pax gene.

When the agent according to the invention is used as an antisense nucleic acid molecule to inhibit gene expression, it is preferably a RNA which, if necessary, can contain modified bases in order to increase its stability in the body to degradation by ribonucleases.

The application of the agent according to the invention as a molecular probe or/and as a therapeutic agent for the inhibition of gene expression is carried out in a manner known to a person skilled in the area of molecular biology.

The invention also concerns a therapeutic or diagnostic agent which is characterized in that it contains at least one Pax protein as the active substance. The Pax protein is preferably selected from the group comprising Pax-1, Pax-2, Pax-3, Pax-4, Pax-5, Pax-6, Pax-7, Pax-8, HuP1, HuP2, HuP48, prd, BSH4, BSH9, Pox neuro and Pox meso. The amino acid sequence of these proteins is shown in the aforementioned publications which were mentioned in connection with the nucleic acid sequence. Human Pax proteins are particularly preferred.

The agent is preferably used in tumour diagnostics or/and tumour therapy.

Yet a further subject matter of the present invention is a therapeutic or diagnostic agent which is characterized in that it contains at least one antibody against a Pax protein as the active substance. Antibodies are preferred which are directed towards one or several Pax proteins from the group comprising Pax-1, Pax-2, Pax-3, Pax-4, Pax-5, Pax-6, Pax-7, Pax-8, HuP1, HuP48, prd, BSH4, BSH9, Pox neuro and Pox meso. Antibodies against human Pax proteins are particularly preferred.

The antibodies according to the invention are preferably monoclonal antibodies which are obtainable via the well-known Köhler-Millstein method i.e., by immunizing an experimental animal, preferably a mouse, with the appropriate Pax protein or/and a mixture of Pax proteins, isolating antibody-producing B cells or spleen cells from the immunized experimental animal and subsequently fusing the antibody-producing cells with a suitable leukemia cell to produce hybridomas. Examples of suitable antibodies are Pax-1, Pax-2 and Pax-6 specific antibodies (FIG. 2).

The antibodies according to the invention can be preferably used in vitro or/and in vivo as agents in tumour diagnostics or/and tumour therapy. In this connection the antibodies can also be used as fragments (e.g. Fab or F(ab)$_2$ fragments) and if desired, coupled to a detectable group (enzyme, fluorescent marker, radioactive marker, nuclear resonance marker etc.) or to a toxin (e.g. ricin, diphtheria toxin etc.). The production of such antibody derivatives is carried out in a manner well-known to a person skilled in the area of immunology (e.g. by covalent coupling via a bi-functional linker).

DETAILED DESCRIPTION OF PREFERRED EMBODIMENTS

Example

1. Examined Pax Proteins

Figure 1:
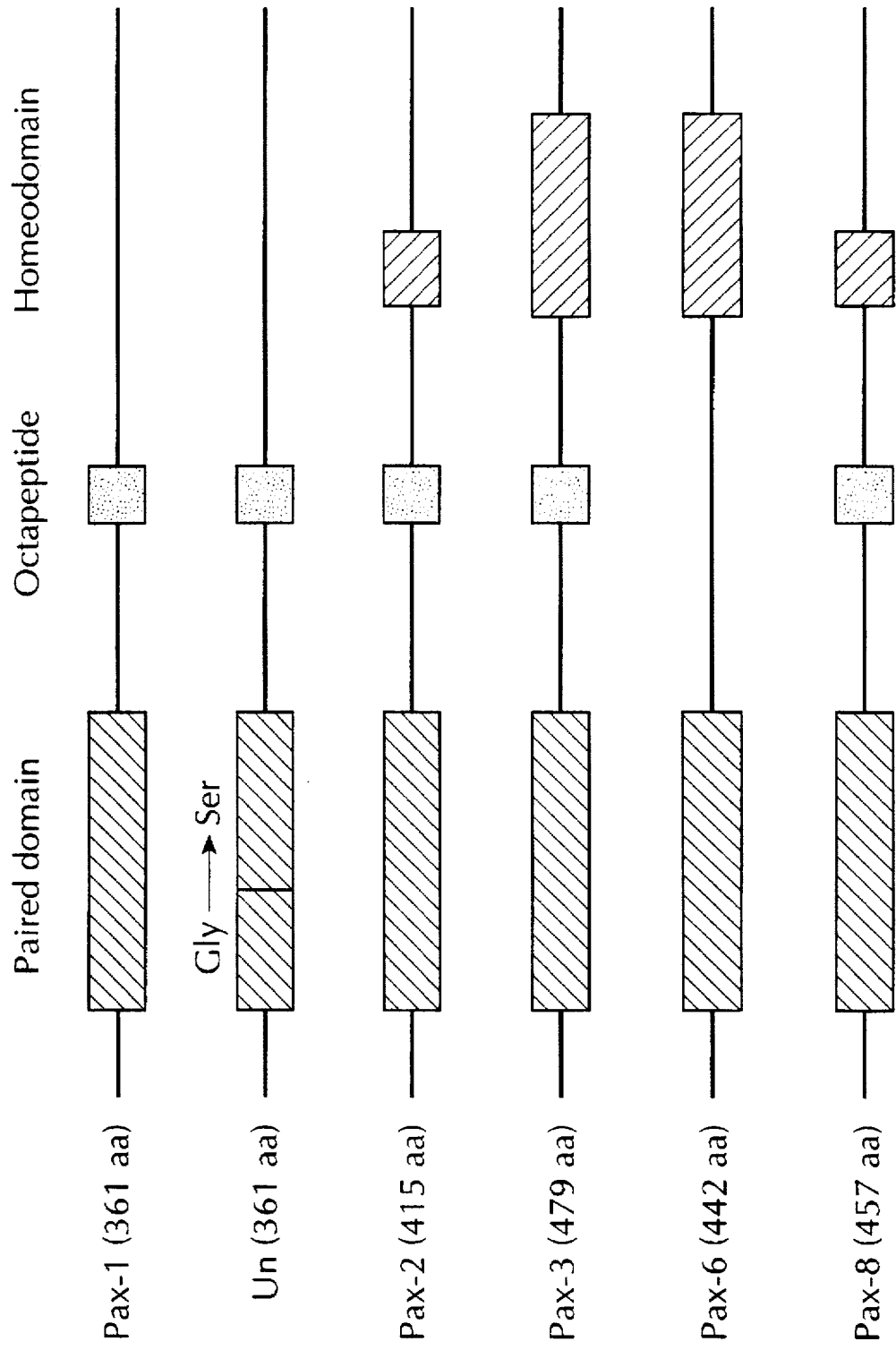
FIG. 1 shows the schematic structure of the examined Pax proteins Pax-1, Pax-2, Pax-3, Pax-6 and Pax-8 and of the mutagenized Pax protein Un.

The effect of the proteins Pax-1, Pax-2, Pax-3, Pax-6 and Pax-8 and of a mutagenized Pax protein (Un) was examined. The schematic structure of these Pax proteins is shown in FIG. 1. The conserved domains within the proteins are shown as bars which also give their approximate positions within the open reading frames. Pax-1 is the only Pax protein which is known to have a complete absence of the homeodomain. Pax-3 and Pax-6 contain complete homeodomains in addition to the "paired" domain. Both DNA binding motifs are separated from one another by at least 100 amino acids. The proteins Pax-2 and Pax-8 only contain 23 amino acids of the a helix of the homeodomain. The point mutation of G to A in the gene coding for the Un protein is characterized by the resulting exchange of Gly by Ser. The nucleotide and amino acid sequences are disclosed by Deutsch et al. (Cell 53 (1988), 617–625) for Pax-1, by Dressler et al. (Development 109 (1990), 787–795) for Pax-2, by Goulding et al. (EMBO J. 10 (1991), 1135–1147) for Pax-3, by Walther and Gruss (Development 113 (1991), 1435–1439) for Pax-6 and by Plachov et al., (Development 110 (1990), 643–651) for Pax-8.

2. Transformation Test

Pax cDNAs were inserted into the multiple cloning site of the vector pCMV5 (Anderson et al., J. Biol. Chem. 264 (1989), 8222–8229). These constructs were cotransfected together with pGKneo as a selectable marker (Soriano et al., Cell 64 (1991), 693–702) in 208 cells and NIH 3T3 cells. The 208 cells were cultured in DMEM (Biochrome) with addition of 10% fetal calf serum (Boehringer Mannheim). The NIH 3T3 cells were cultured in DMEM containing 5% new-born calf serum (Boehringer Mannheim). 2 μg of the respective pCMV-Pax expression plasmid was transfected together with 1 μg pGKneo and 7 μg carrier DNA on 70% confluent single cell layers of a 100 mm tissue culture plate using the calcium phosphate method with modifications (Weber and Schaffner, Nature 315 (1984), 75–77). The transfected cells were divided into three groups after 24 hours. One group was allowed to stand for 2 to 4 weeks depending on the beginning of focus formation. Afterwards the cells were stained with a few drops of glutaraldehyde and with 1% methylene blue in water. The tissue culture plates were rinsed with water and the foci were counted.

A further third of the cells were either sown in 0.6%, 0.9% or 1.2% soft agar as described by Fidler et al., Anticancer Res. 11 (1991), 17–24. The remaining third was selected for DNA uptake by addition of G418 (Gibco) 24 hours after the shock of the cells. In the case of the 208 cells, 0.4 mg/l G418 and in the case of NIH 3T3 cells 0.6 mg/ml G418 was added. The morphologically transformed foci were picked out and subsequently cultured. These cell isolates were propagated by continuous incubation in the selection medium and used for expression analysis and the transformation tests.

3. Results of the Transformation Tests

The results of a transformation of 208 cells with Pax proteins is shown in Table 1. The left column lists the DNAs which were introduced into the cells. pCMV denotes cells which only contain a pCMV construct as a negative control, pSV is the T antigen (SV40 virus) expression construct used as a positive control. The various pCMV Pax expression constructs are indicated by the name of the Pax protein which they express. The growth of the cells was tested in 0.6%, 0.9% and 1.2% soft agar. The cell colonies were counted 2 to 3 weeks after plating. The experiments were carried out at least twice for each cell type. + denotes growth in soft agar, − denotes no growth, +− denotes contradictory results in two experiments.

The next column lists whether the corresponding transformed cells were able or not to induce focus formation when mixed with normal 208 cells. This mix experiment was carried out twice.

The last column shows the number of injected nude mice and the number of injections which led to tumour formation. For this, male nude NMRI mice at an age of 4 weeks were injected subcutaneously in the flank with 1 to $5\times10^5$ transformed cells. The cells were trypsinized and washed twice with phosphate-buffered salt solution before injection in order to exclude stimulating effects from the serum. The animals were examined on a weekly basis for a maximum of three months for the formation of tumours.

TABLE 1

| Transfected DNA | Soft agar test | | | Focus test | Tumorigenicity number of injections/ number of tumours in nude mice |
|---|---|---|---|---|---|
| | 0.6% | 0.9% | 1.2% | | |
| pCMV | −+ | − | − | − | 5/0 |
| pSV | ++ | ++ | ++ | + | 6/6 |
| Pax-1 | ++ | ++ | ++ | + | 6/6 |
| Un | −+ | − | | − | 6/1 |
| Pax-2 | ++ | ++ | ++ | + | 6/6 |
| Pax-3 | ++ | −+ | ++ | + | 6/6 |
| Pax-6 | ++ | ++ | ++ | + | 6/4 |
| Pax-8 | ++ | ++ | ++ | + | 6/6 |

The results in Table 1 show the oncogenic potential of Pax genes and of the "paired" domain. In the test which shows the clones expressing various Pax proteins in soft agar at different concentrations, the growth at increasing concentrations of soft agar can be related to the probability of the occurrence of tumours. Cells which only contained the pCMV expression vector showed no growth in 0.6% soft agar or more. Cells which expressed the Pax-1, Pax-2, Pax-3, Pax-6 or Pax-8 protein could in contrast grow at concentrations of up to 1.2% soft agar. Growth in this semi-solid medium shows that the Pax proteins impart the cells with the ability for anchor-independent growth. The mutated Un protein was not able to completely transform these cells which is apparent from the absence of anchor-independent growth at higher soft agar concentrations.

The tumours produced by injection of pCMV-Pax expression constructs were analyzed by standard in situ hybridization protocols (Goulding, EMBO J. 10 (1991), 1135–1147). The cells in the Pax tumours are spindle-shaped. The tumours are well provided with vessels and exhibit a strong extracellular matrix production. All tumours were solid and encapsulated.

In addition a methylene blue test was carried out in order to determine the ability of the cells to overcome contact inhibition. This test was carried out twice in untreated cells after transfection. Cells which had taken up the transforming DNA are able to grow over non-transformed cells which results in darkly marked cell foci. The formation of cell foci was observed in the cells transformed with Pax genes—as in the positive control with pSV—whereas in the cells transformed with the negative control pCMV and and in the non-transformed cells (208 and NIH 3T3 cells) considerably fewer foci were visible.

The results of the soft agar test are in agreement with the occurrence of strongly stained foci in the methylene blue test in the case of 208 and NIH 3T3 cell transfections using Pax proteins which contain functional "paired" domains, and with tumour formation in the nude mouse.

4. Immunological Detection of Pax Expression in Transfected Cells

Figure 2:
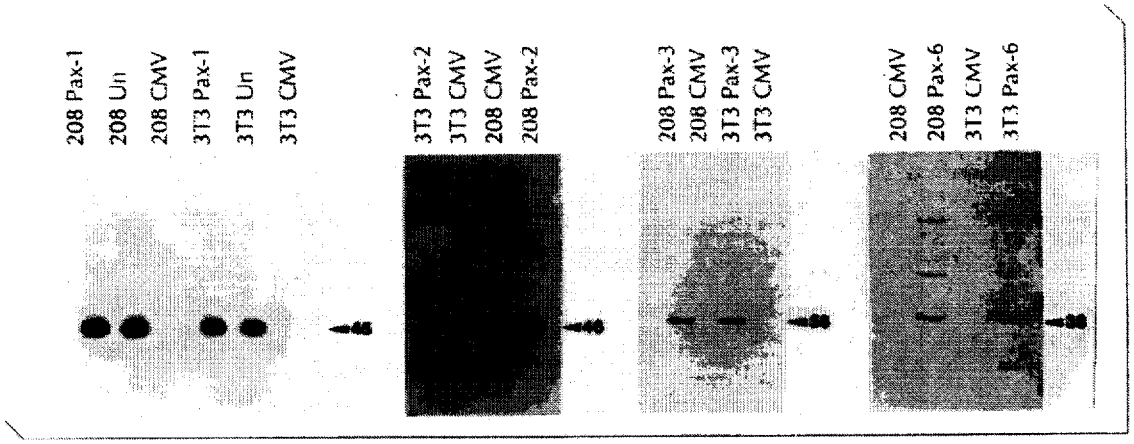
FIG. 2 shows Western blots of cell extracts expressing Pax protein after incubation with specific antibodies and enzymatic detection of the antibody-protein binding.

Total cell extracts were prepared from the NIH 3T3 cells and 208 cells transfected according to point 2 supra using known protocols (Balling et al., Cell 55, (1988), 531–535). After determination of the protein concentration, 50 μg of each cell extract was separated on a 12.5% SDS polyacrylamide gel and transferred to an Immobilon P membrane by semi-dry electical transfer. The membrane was blocked in 5% dry milk powder/phosphate-buffered salt solution and incubated overnight with a 1:200 dilution of the respective Pax antibodies and developed with the peroxidase/ diaminobenzidine reaction (Balling et al., Supra). It can be seen from FIG. 2 that antibodies against Pax-1, Pax-2, Pax-3 and Pax-6 showed a reaction with the corresponding transfected cells. The Pax-2 antibody showed a cross-reaction with Pax-8 and enabled a confirmation of the Pax-8 expression with the respective cell extracts (not shown). The molecular weight of the Pax proteins was determined by comparison with the rainbow protein marker (Amersham). The apparent molecular weight of the proteins is given in kD. 208 as well as NIH 3T3 cell extracts contained about equal amounts of the respective Pax proteins per 50 μg cell extracts. This shows that the CMV promoter functions equally well in both cell lines. The Western blot of Pax-1 shows that Pax-1 and the mutated Un protein are expressed in about equal amounts. A further cell extract which had been prepared by transfection of cells with a pSV40 promoter/Pax-1 construct contained even higher amounts of the Pax protein. In all cases the Western blots showed that the control cells transfected with pCMV produced very much less or no detectable amounts of protein.

We claim:

1. A method for determining presence of a transformed cell in a sample comprising contacting said sample with a nucleic acid probe which specifically hybridizes to a gene which encodes a protein selected from the group consisting of Pax-1, Pax-3, Pax-4, Pax-5, Pax-6, Pax-7, Pax-8, HuP1, HuP2, HuP48, prd, BSH5, BSH9, Pox neuro and Pox mesa, or with an antibody which specifically binds to the encoded protein, wherein expression of said gene or presence of said protein is indicative of a transformed cell in said sample.

2. The method of claim 1, wherein said gene is Pax-1, Pax-3, Pax-4, Pax-5, Pax-6, Pax-7 or Pax-8.

3. The method of claim 1, comprising determining said expression by contacting said sample with a nucleic acid probe which hybridizes to said at least one gene.

4. The method of claim 3, wherein said at least one nucleic acid molecule comprises at least one nucleotide sequence selected from the group consisting of:

(i) a nucleotide sequence encoding amino acids 5 to 19 of a paired domain of a Pax protein, (ii) a nucleotide sequence encoding amino acids 35 to 41 of a paired domain of a Pax protein, (iii) a nucleotide sequence encoding amino acids 68 to 74 of a paired domain of a Pax protein, (iv) a nucleotide sequence encoding amino acids 95 to 100 of a paired domain of a Pax protein, and (v) a nucleotide sequence which encodes amino acids 115 to 120 of a paired domain of a Pax protein;

wherein said Pax protein is selected from the group consisting of Pax-1, Pax-3, Pax-4, Pax-5, Pax-6, Pax-7, Pax-8, HuP1, HuP2, HuP48, prd, BSH5, BSH9, Pax neuro and Pax meso.

5. The method of claim 4, wherein said at least one nucleic acid molecule comprises all of (i), (ii), (iii), (iv) and (v).

6. The method of claim 3, wherein said at least one nucleic acid probe is from 10 to 100 nucleotides in length.

7. The method of claim 6, wherein said nucleic acid probe is 12 to 50 nucleotides in length.

8. The method of claim 3, wherein said nucleic acid probe comprises a nucleotide sequence which encodes amino acids 1–74 of a paired domain of the protein encoded by said at least one gene.

9. The method of claim 2, comprising determining said expression by contacting said sample with an antibody fragment which specifically binds to said protein.

10. The method of claim 9, wherein said antibody is a monoclonal antibody.

11. The method of claim 9, wherein said antibody is coupled to a detectable group.

12. The method of claim 9, wherein said antibody specifically binds to a Pax protein selected from the group consisting of Pax-1, Pax-2 and Pax-6.

13. A method for determining if a cell synthesizes an oncoprotein which induces cell proliferation, anchor independent growth, and angiogenesis, comprising assaying said cell to determine if a Pax gene is expressed thereby, wherein expression of said Pax gene is indicative of a cell which exhibits signs of malignancy, said signs comprising contact inhibition in a focus assay, growth in soft agar, and tumor induction in a nude mouse.

* * * * *

UNITED STATES PATENT AND TRADEMARK OFFICE
CERTIFICATE OF CORRECTION

PATENT NO.  : 5,747,250
DATED       : May 5, 1998
INVENTOR(S) : Peter Gruss, et. al.

It is certified that error appears in the above-indentified patent and that said Letters Patent is hereby corrected as shown below:

In column 1, line 55, after "desired" add --, the active agent can be used--.

In column 4, line 27, change "a" to the Greek letter --α--.

In Claim 1, column 6, line 52, change "mesa" to --meso--.

In Claim 1, column 6, line 62, change "molecule" to --probe--.

Signed and Sealed this

Tenth Day of April, 2001

Attest:

NICHOLAS P. GODICI

*Attesting Officer*          *Acting Director of the United States Patent and Trademark Office*